United States Patent [19]
Lapidus et al.

[11] Patent Number: 6,146,828
[45] Date of Patent: Nov. 14, 2000

[54] METHODS FOR DETECTING DIFFERENCES IN RNA EXPRESSION LEVELS AND USES THEREFOR

[75] Inventors: Stanley N. Lapidus, Bedford, N.H.; Anthony P. Shuber, Milford, Mass.

[73] Assignee: Exact Laboratories, Inc., Maynard, Mass.

[21] Appl. No.: 09/110,759

[22] Filed: Jul. 3, 1998

Related U.S. Application Data

[63] Continuation-in-part of application No. 08/876,857, Jun. 16, 1997, Pat. No. 5,928,870, which is a continuation-in-part of application No. 08/700,583, Aug. 14, 1996, Pat. No. 5,670,325.

[51] Int. Cl.[7] .................................................. C12Q 1/68
[52] U.S. Cl. ............................................. 435/6; 536/245
[58] Field of Search ............................... 435/6; 536/24.5, 536/23.1

[56] References Cited

U.S. PATENT DOCUMENTS

| | | |
|---|---|---|
| 4,101,279 | 7/1978 | Aslam . |
| 4,309,782 | 1/1982 | Paulin . |
| 4,333,734 | 6/1982 | Fleisher . |
| 4,445,235 | 5/1984 | Slover et al. . |
| 4,535,058 | 8/1985 | Weinberg et al. . |
| 4,683,195 | 7/1987 | Mullis et al. . |
| 4,705,050 | 11/1987 | Markham . |
| 4,735,905 | 4/1988 | Parker . |
| 4,786,718 | 11/1988 | Weinberg et al. . |
| 4,857,300 | 8/1989 | Maksem . |
| 4,871,838 | 10/1989 | Bos et al. . |
| 4,981,783 | 1/1991 | Augenlicht . |
| 4,982,615 | 1/1991 | Sultan et al. . |
| 5,087,617 | 2/1992 | Smith . |
| 5,126,239 | 6/1992 | Livak et al. . |
| 5,137,806 | 8/1992 | LeMaistre et al. . |
| 5,149,506 | 9/1992 | Skiba et al. . |
| 5,196,167 | 3/1993 | Guadagno et al. . |
| 5,248,671 | 9/1993 | Smith . |
| 5,272,057 | 12/1993 | Smulson et al. . |
| 5,302,509 | 4/1994 | Cheeseman . |
| 5,330,892 | 7/1994 | Vogelstein et al. . |
| 5,331,973 | 7/1994 | Fiedler et al. . |
| 5,348,855 | 9/1994 | Dattagupta et al. . |
| 5,352,775 | 10/1994 | Albertsen et al. . |
| 5,362,623 | 11/1994 | Vogelstein et al. . |
| 5,369,004 | 11/1994 | Polymeropoulos et al. . |
| 5,378,602 | 1/1995 | Polymeropoulos et al. . |
| 5,380,645 | 1/1995 | Vogelstein . |
| 5,380,647 | 1/1995 | Bahar . |
| 5,382,510 | 1/1995 | Levine et al. . |
| 5,409,586 | 4/1995 | Kamahori et al. . |
| 5,458,761 | 10/1995 | Kamahori et al. . |
| 5,463,782 | 11/1995 | Carlson et al. . |
| 5,466,576 | 11/1995 | Schulz et al. . |
| 5,468,610 | 11/1995 | Polymeropoulos et al. . |
| 5,468,613 | 11/1995 | Erlich et al. . |
| 5,489,508 | 2/1996 | West et al. . |
| 5,492,808 | 2/1996 | de la Chapelle et al. . |
| 5,496,470 | 3/1996 | Lenhart . |
| 5,508,164 | 4/1996 | Kausch et al. . |
| 5,512,441 | 4/1996 | Ronal . |
| 5,514,547 | 5/1996 | Balazs et al. . |
| 5,527,676 | 6/1996 | Vogelstein et al. . |
| 5,532,108 | 7/1996 | Vogelstein . |
| 5,580,729 | 12/1996 | Vogelstein . |
| 5,670,325 | 9/1997 | Lapidus et al. ............................. 435/6 |
| 5,709,998 | 1/1998 | Kinzler et al. . |
| 5,928,870 | 7/1999 | Lapidus et al. ............................. 435/6 |

FOREIGN PATENT DOCUMENTS

| | | |
|---|---|---|
| 11325/95 | 10/1994 | Australia . |
| 0 284 362 A2 | 9/1988 | European Pat. Off. . |
| 0 337 498 | 10/1989 | European Pat. Off. . |
| 0 390 323 A2 | 10/1990 | European Pat. Off. . |
| 0 390 323 A3 | 10/1990 | European Pat. Off. . |
| 0 407 789 A1 | 1/1991 | European Pat. Off. . |
| 0 407 789 B1 | 1/1991 | European Pat. Off. . |
| 0 608 004 A2 | 7/1994 | European Pat. Off. . |
| 0 259 031 B1 | 11/1994 | European Pat. Off. . |
| 0 664 339 A1 | 7/1995 | European Pat. Off. . |
| WO90/09455 | 8/1990 | WIPO . |
| WO 92/13103 | 8/1992 | WIPO . |
| WO92/16657 | 10/1992 | WIPO . |
| WO 93/18186 | 9/1993 | WIPO . |
| WO 93/20233 | 10/1993 | WIPO . |
| WO 94/00603 | 1/1994 | WIPO . |
| WO 94/09161 | 4/1994 | WIPO . |
| WO 94/10575 | 5/1994 | WIPO . |
| WO 94/11383 | 5/1994 | WIPO . |
| WO 95/07361 | 3/1995 | WIPO . |
| WO 95/09928 | 4/1995 | WIPO . |
| WO 95/09929 | 4/1995 | WIPO . |

(List continued on next page.)

OTHER PUBLICATIONS

Bos et al., Nature 327:293–297, May 1987.

Sanger F., S. Nicklen and A.R. Coulson (Dec. 1977) "DNA sequencing with chain–terminating inhibitors" vol. 74, No. 12 *Proc. Natl. Acad. Sci. USA* pp. 5463–5467.

Wallace R.B., et al. (1979) "Hybridization of synthetic Oligodeoxyribonucleotides to Φx 174 DNA: the effect of single base pair mismatch" vol. 6, No. 11 *Nucleic Acids Research* pp. 3543–3557.

Coll P., K. Phillips, and F. C. Tenover (Oct. 1989) "Evaluation of a Rapid Method of Extracting DNA from Stool Samples for use in Hybridization Assaya" vol. 27, No. 10 *Journal of Clinical Microbiology* pp. 2245–2248.

Jessup J. M. and G. E. Gallick (Sep./Oct. 1992) "The Biology of Colorectal Carcinoma" *Current Problems in Cancer* pp. 263–328.

Litia A., L. Liukkonen and H. Siitari (1992) "Simultaneous detection of two cystic fibrosis alleles using dual–label time–resolved fluorometry" 6*Molecular and Cellular Probes* pp. 505–512.

(List continued on next page.)

*Primary Examiner*—Scott W. Houtteman
*Attorney, Agent, or Firm*—Testa, Hurwitz & Thibeault, LLP

[57] ABSTRACT

Methods are disclosed for the detection and diagnosis of disease by determining differences in the number of RNA molecules in a patient sample compared to an expected number.

5 Claims, 2 Drawing Sheets

FOREIGN PATENT DOCUMENTS

| | | |
|---|---|---|
| WO 95/12606 | 5/1995 | WIPO . |
| WO 95/13397 | 5/1995 | WIPO . |
| WO 95/15400 | 6/1995 | WIPO . |
| WP 95/16792 | 6/1995 | WIPO . |
| WO 95/18818 | 7/1995 | WIPO . |
| WO 95/19448 | 7/1995 | WIPO . |
| WO 95/19948 | 7/1995 | WIPO . |
| WO 95/25813 | 9/1995 | WIPO . |
| WO 95/31728 | 11/1995 | WIPO . |
| WO 96/01907 | 1/1996 | WIPO . |
| WO 96/06951 | 3/1996 | WIPO . |
| WO 96/08514 | 3/1996 | WIPO . |
| WO 96/12821 | 5/1996 | WIPO . |
| WO 96/13611 | 5/1996 | WIPO . |
| WO97/09449 | 3/1997 | WIPO . |

OTHER PUBLICATIONS

Young G. P., and B.H. Demediu (1992) "The genetics, epidemiology, and early detection of gastrointestinal cancers" 4 *Current Opinion in Oncology* pp. 728–735.

Hoss M., et al. (Sep. 17, 1992) "Excrement analysis by PCR" *Scientific Correspondence* p. 199.

Sidransky, et al. (Apr. 3, 1992) "Identification of ras Oncogene Mutations in the Stool of Patients with Curable Colorectal Tumors"vol. 256 *Science* pp. 102–105.

Takeda S., S. Ichii, and Y. Nakamura (1993) "Detection of K–ras Mutation in Sputum by Mutant–Allele–Specific Amplification (MASA)" 2 *Human Mutation*pp. 112–117.

Leong P.K., et al. (1993) "Detection of MYCN Gene Amplification and Deletions of Chromosome 1p in Neuroblastoma by In Situ Hybridization Using Routine Histologic Sections " vol. 69, No.1 *Laboratory Investigations* pp. 43–50.

Thibodeau S.N., G. Bren, D. Schaid (May 7, 1993) "Microsatellite Instability in Cancer of the Proximal Colon" vol. 260 *Science* pp. 816–819.

Naber S. P.(Dec. 1, 1994) "Molecular Pathology —Detection of Neoplasia" 331 *New England Journal of Medicine* pp. 1508–1510.

Cave H., et al. (1994) "Reliability of PCR Directly from Stool Samples: Usefulness of an Internal Standard" vol. 16, No. 5 *BioTechniques* pp. 809–810.

Caldas C., et al (Jul. 1, 1994) "Detection of K–ras Mutations in the Stool of Patients with Pancreatic Adenocarcinoma and Pancreatic Ductal Hyperplasia" 54 *Cancer Research* pp. 3568–3573.

Charlesworth B., P. Sniegowski and W. Stephan (Sep. 15, 1994) "The evolutionary dynamics of repetitive DNA in eukaryotes" vol. 371 *Nature* pp. 215–220.

Fearon E. R.(1995) "16 Molecular Abnormalities in Colon and Rectal Cancer" *The Molecular Basis of Cancer* pp. 340–357.

Ravelingien N., J. C. Pector & T. Velu (1995) "Contribution of molecular oncology in the detection of colorectal carcinomas" 58 *Acta Gastro–Enterologica Belgica* pp. 270–273.

Duffy M.J.(1995) "Can Molecular Markers now be used for Early Diagnosis of Malignancy?" 41/10*Clin. Chem.* pp. 1410–1413.

Blum H.E.(1995) "Colorectal Cancer: Future Population Screening for Early Colorectal Cancer" vol. 31A *European Journal of Cancer*, pp. 1369–1372.

Ridanpaa M., S. Anttila and K. Husgafvel–Pursiainen (1995) "Detection of Loss of Heterozygosity in the p53 Tumor Suppressor Gene Using a PCR–based Assay" 191 *Path. Res. Pract.* pp. 399–402.

Smith–Ravin J., J. England, I.C. Talbot, W. Bodmer (1995) "Detection of c–Ki–ras mutations in faecal samples from sporadic colorectal cancer patients" 36 *Gut* pp.81–86.

Orlow I., et al. (Oct. 18, 1995) "Deletion of the p16 and p15 Genes in Human Bladder Tumors" vol. 87, No. 20 *Journal of the National Cancer Institute* pp. 1524–1529.

Hasegawa, Y., et al., (1995) "Detection of K–ras mutations in DNAs isolated from feces of patients with colorectal tumors by mutant–allel–specific amplification (MASA)" 10 *Oncogene* pp. 1441–1445.

Loktionov A. and I. K. O'Neill (1995) "Early detection of cancer–associated gene alterations in DNA isolated from rat feces during intestinal tumor induction with 1,2–dimethylhydrazine" 6 *International Journal of Oncology* pp. 437–445.

Honchel R., K. C. Halling and S. N. Thibodeau (1995) "Genomic instability in neoplasia" vol. 6 *Seminars in Cell Biology* pp. 45–52.

Deuter R., S. Pietsch, S. Hertel and O. Muller (1995) "A method for preparation of fecal DNA suitable for PCR" vol. 23, No. 18 *Nucleic Acids Research* pp. 3800–3801.

Dib C., et al. (Mar. 14, 1996) "A comprehensive genetic map of the human genome based on 5,264 microsatellites" vol. 380 *Nature* pp. 152–154.

Cunningham C. and M.G. Dunlop (1996) "Molecular genetic basis of colorectal cancer susceptibility" 83 *British Journal of Surgery* pp. 321–329.

Mao L., et al. (Feb. 2, 1996) "Molecular Detection of Primary Bladder Cancer by Microsatellite Analysis" vol. 271 *Science* pp. 659–662.

Villa E., et al. (May 1996) "Identification of Subjects at Risk for Colorectal Carcinoma through a Test Based on k–ras Determination in the Stool" vol. 110, No. 5 *Gastroenterology* pp. 1346–1353.

Nollau P., C. Moser, G. Weinland, and C. Wagener (1996) "Detection of K–ras Mutations in Stools of Patients with Colorectal Cancer by Mutant–enriched PCR" 66 *Int. J. Cancer* pp. 332–336.

Eguchi S., N. Kohara, K. Komuta, and T. Kanematsu (Apr. 15, 1996) "Mutations of the p53 Gene in the Stool of Patients with Resectable Colorectal Cancer" vol. 77, No. 8 *Cancer Supplement* pp. 1707–1710.

Nollau P., C. Moser, and C. Wagener (May 1996) "Isolation of DNA from Stool and Bodily Fluids for PCR Amplication" vol. 20, No. 5 *BioTechniques* pp. 784–788.

Rhyu M. S. (Mar. 6, 1996) "Molecular Mechanisms Underlying Hereditary Nonpolyposis Colorectal Carcinoma" vol. 88, No. 5 *Journal of the National Cancer Institute* pp. 240–251.

Gyllensten U. B., Allen M. (1995) "Sequencing of Vitro Amplified DNA" in *Recombinant DNA Methodology II* (Wu, ed) pp. 565–578.

Myers, R.M., "The Pulses of Subtraction", vol. 259 Science, pp. 942–943 (1993).

Johnson et al., From Mutation mapping to Phenotype cloning: vol. 92 Proc. Natl. Sci. USA, pp. 83–85 (1995).

Watson et al. "Isolation of Differentiality Expressed Sequence Tags from Human Breast Cancer" Advanced in Brief XP 000576043, pp. 4598–4602.

Bos et al. (May 1997) "Prevalence of ras Gene Mutations in Human Colorectal Cancers" vol. 327 Nature, pp. 293–297.

Segel (1976) "Double Label Analysis," *Biochemical Calculations*, pp. 373–376.

METHODS FOR DETECTING DIFFERENCES IN RNA EXPRESSION LEVELS AND USES THEREFOR

This application is a continuation-in-part of U.S. Ser. No. 08/876,857 filed Jun. 16, 1997, now U.S. Pat. No. 5,928,870, which is a continuation-in-part of U.S. Ser. No. 08/700,583, filed Aug. 14, 1996, (issued as U.S. Pat. No. 5,670,325).

FIELD OF THE INVENTION

This invention relates to methods useful for disease diagnosis by detecting the presence of differences in RNA expression levels in cellular samples.

BACKGROUND OF THE INVENTION

Early disease diagnosis, especially in diseases such as cancer, is of central importance to halting disease progression, and reducing morbidity. Diagnostic disease research typically has focused on specific mutations in DNA that result in lost or modified cellular activities. For example, considerable research has focused on DNA mutations associated with cancer. Cancer is a disease thought to be characterized by genomic instability. Generally, genomic instability defines a broad class of disruptions in genomic nucleotide sequences. Numerous genomic instabilities have been associated with cancer. For example, mutations in a number of oncogenes and tumor suppressor genes have been implicated in tumorigenesis. Duffy, Clin. Chem., 41: 1410–1413 (1993). In addition, the loss of heterozygosity at the P53 tumor suppressor locus has been correlated with various types of cancer. Ridanpaa, et al., Path. Res. Pract, 191: 399–402 (1995). The loss or other mutation of the apc and dcc tumor suppressor genes has also been associated with tumor development. Blum, Europ. J. Cancer, 31A: 1369–372 (1995). Finally, tumorigenesis has also been correlated with microsatellite instability. Genetic changes characteristic of genomic instability theoretically can serve as markers for the early stages of, for example, color cancer, and can be detected in DNA isolated from biopsied colonic epithelium and in some cases from transformed cells shed into fecal material. Sidransky, et al., Science, 256: 102–105 (1992).

While DNA-based diagnostics provide useful information concerning genomic disruptions associated with disease, such tests are not necessarily informative with respect to DNA expression. Some researchers have attempted to measure DNA expression by looking for changes in cellular protein content. Increased protein expression results in markers characteristic of various diseases. For example, the protein, prostate-specific antigen, has been used as a diagnostic marker for prostate cancer. Similarly, carcinoemrbyonic antigen has been used as a marker of colorectal cancer. Such protein markers generally are indicative of a late stage in the etiology of the disease. Often, by the time such markers are detected, the associated disease has progressed to a state that is difficult to treat or cure. Accordingly, there is a need in the art for methods for early detection of changes in gene expression that are indicative of disease.

SUMMARY OF THE INVENTION

The present invention provides methods for disease detection by analysis of RNA expression. The invention also provides methods for identifying genes associated with disease based upon differential RNA expression. Such methods detect the presence in a biological sample of levels of RNA indicative of disease in a subpopulation of cells in the sample, or indicative of an inherited disease or predisposition thereto. In particular, methods of the invention are useful for detecting small changes in RNA expression (levels of RNA in a sample) that are indicative of the presence of disease in the patient from whom a sample has been obtained. Practice of the invention permits, for example, detection of a small increase or decrease in RNA expressed from a gene whose overexpression or underexpression (compared to a reference gene) is associated with disease or the predisposition for a disease.

In general, the invention comprises the enumeration of two RNA species. The expression level of a first, reference, RNA does not change depending on the disease state of the patient (i.e., the numbers of the RNA are identical in both diseased and non-diseased cells in a sample). The expression level of a second, target, RNA changes in diseased cells (i.e., its number in a sample taken from a patient with a disease is either more or less than the number expected in a healthy sample). If the ratio of the two RNA species is the same in both a patient sample and a known healthy sample, the patient does not have the indicia of disease. However, if the ratio is statistically-significantly different in a patient sample and a healthy standard, the patient is diagnosed as having a disease or a predispostion therefor. The ratio of RNA in a healthy sample may be empirically determined for each assay, may be determined from a healthy tissue sample, or may be standardized through measurement of numerous healthy samples. If a standard is used for comparison of the ratios, only the reference and target RNA in a patient sample need be measured (i.e., a separate measurement of healthy tissue or body fluid need not be taken).

Hybridization probes are used to detect the presence of each RNA. If the number of hybridization events involving the two RNAs is different, the difference may be due to insignificant background or it may be due to a statistically-significant difference in the quantities of the two RNAs in the population from which the sample was drawn. In the latter case, the difference can be correlated, to a degree of defined statistical confidence, with the presence in the sample of diseased cells.

In a preferred embodiment, methods of the invention comprise diagnosing a disease by determining, in a patient sample, the ratio of a reference RNA, the expression of which is not altered in a diseased cell, to a target RNA, the expression of which is expected to be altered in a diseased cell; and comparing that ratio to the ratio of the reference and target RNAs expected in a sample in which disease is not present. The presence of statistically-significant difference is indicative of the presence of diseased cells in the patient sample.

Also in a preferred embodiment, methods are provided for detecting a difference in RNA expression between first and second samples. Such methods comprise the comparing 1) a ratio of a first RNA and a second RNA in a first sample with 2) the ratio of the first and second RNAs in a second sample.

Preferred methods also include identification of a gene, the expression of which is associated with a disease. Methods for identification of a disease-associated gene according to the invention comprise comparing the ratio, in a patient sample, of an RNA expression product of the disease-associated gene to an RNA expression product of a reference gene that is not affected by disease, with the ratio of the disease-associated gene and reference gene in a non-diseased sample. The presence of a statistically-significant difference between the ratios being indicative of a gene, the expression of which is associated with disease.

A method of the invention for determining predisposition to a disease comprises determining a ratio of RNA expressed by a paternal allele to RNA expressed by a maternal allele; wherein the patient is predisposed to the disease if there is a statistically-significant difference between the determined ratio and the expected ratio of 1.0.

In a specifically-preferred embodiment, methods of the invention further comprise the step of isolating RNA from other components of a biological sample. Especially preferred are methods in which mRNA is isolated by, for example, using an oligo-dT column. In a further preferred embodiment, methods of the invention further comprise the step of reverse-transcribing RNA in a sample, whether isolated or not, and optionally constructing a cDNA library. Prior to counting RNA or cDNA molecules, it is preferred to amplify the molecules of interest (e.g., target and reference RNAs) by, for example, polymerase chain reaction. Counting preferably is accomplished using detectably-lableled hybridization probes which bind specifically with their RNA or cDNA complements. First and second RNAs are preferably distinguished using p32 and p33 labels, and counting individual radioactive emissions from the two different spectra emitted by those isotopes. A single-base extension assay using a chain-terminating nucleotide, as described below, is also a preferred detection means. Other useful detection moities include flourescent markers, molecular weight tags, impedance markers, and other markers known in the art for detecting nucleic acids.

Useful reference genes in methods of the invention include housekeeping genes, such as beta-globin, alcohol dehydrogenase, or any other gene, the expression of which does not vary depending on the disease status of the cell containing the gene.

Suitable target genes for methods of the invention include any gene, the expression of which is altered prior to or during the course of a disease. For example, oncogenes and tumor supressors, the expression of which is altered during or precedent to oncogenesis, are useful targets for altered RNA expression. Also, the gene for Huntington's disease is a useful target, as expression of that gene is altered coincident with manifestation of the disease. Finally, changes in the number of mitochondrial nucleotides are useful for detection of or for the prediction of onset of Alzheimer's disease.

Methods of the invention are useful to detect the presence of maternal or paternal imprinting, wherein disease results from reduced expression or non-expression of either the maternal or paternal allele at a genetic locus associated with a disease.

Methods of the invention involve counting individual RNA molecules, thus enabling an accurate determination of differences in expression levels using statistical methods, such as those described below. Methods of the invention detect deviations from expected amounts of expressed RNA, whether the deviation is an increase or a decrease from the expected. Thus, methods of the invention are useful not only to detect genes that are turned on during disease progession, but also are useful to detect reduced RNA expression levels associated with a deletion, or other mutation, in DNA, or with genomic alterations, such as microsatellite rearrangements and the like.

Methods of the invention are conducted on any tissue or body fluid sample. Since inventive methods rely on enumeration of specific RNA molecules, the statistical sensitivity of these methods allows one to determine small differences in RNA expression in only a subpopulation of a heterogeneous sample (e.g., stool). However, methods of the invention are also conducted on biopsy tissue, typically containing a high proportion of affected cells, or on other tissue or body fluid samples, such as blood, sputum, semen, and the like.

Further aspects of the invention will become apparent upon consideration of the following detailed description and of the drawings.

DETAILED DESCRIPTION OF THE INVENTION

Figure 1A:
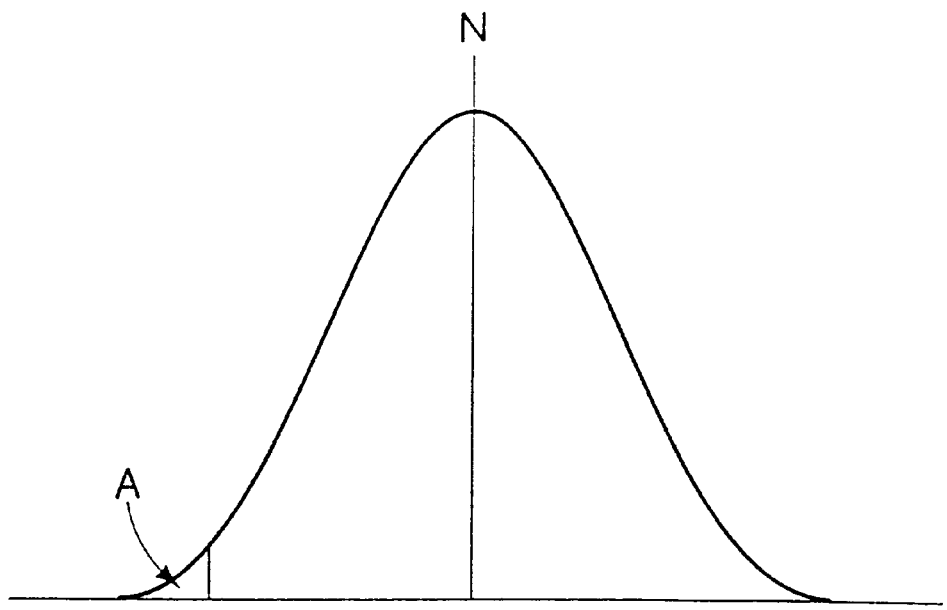
FIGS. 1A and 1B are model Gaussian distributions showing regions of low statistical probability.

Methods of the invention are useful for detecting differences in RNA expression in cells affected by disease, or predisposed to disease. By detecting small changes in RNA expression levels, methods of the invention allow early diagnosis of genetic alterations characteristic of diseases such as cancer, Parkinson's disease, Alzheimer's disease, diabetes, alcoholism, Huntington's disease, and other conditions in which sporadic or inherited alterations of genomic DNA play a role. Methods of the invention are useful for the detection of small changes in RNA expression levels (compared to a reference RNA) in homogeneous cellular samples. According to the present invention, preferred methods are useful for the detection of altered RNA expression in a heterogeneous cellular sample in which the altered expression occurs in only a small subpopulation of cells in the sample. Using traditional detection methods, such a subpopulation would be difficult, if not impossible, to detect— especially if the mutation that is causative of the alteration is unknown at the time of detection or a clonally—impure cellular population is used. Methods of the present invention are capable of detecting alterations in RNA expression levels in a small number of cells in an impure cellular population because such methods rely upon counting individual RNA molecules. Methods of the invention comprise counting a number of an RNA suspected of being overexpressed or underexpressed in association with a disease, and comparing that number with the number of the RNA expected to be expressed by a gene known not to be affected by or causative of the disease. It is not necessary to know the entire sequence of either the target RNA (that suspected to be associated with the disease) or the reference RNA (that known or suspected not to be associated with the disease).

Quantitative sampling of a nucleotide sequence that is uniformly distributed in a biological sample typically follows a Poisson distribution. For large populations, such as the typical number of RNA molecules in a biological sample, the Poisson distribution is similar to a normal (Gaussian) curve with a mean, N, and a standard deviation that may be approximated as the square root of N.

Statistically-significance between ratios of RNA molecules obtained from a biological sample may be determined by any appropriate method. See, e.g., Steel, et al., Principles and Procedures of Statistics, A Biometrical Approach (McGraw-Hill, 1980), the disclosure of which is incorporated by reference herein. An exemplary method is to determine, based upon a desired level of specificity (tolerance of false positives) and sensitivity (tolerance of false negatives) and within a selected level of confidence, the difference between the ratios of target and reference RNAs that must be obtained in order to reach a chosen level of statistical significance. A threshold issue in such a determination is the minimum number, N, of RNAs (for each of target and reference) that must be available in a population in order to allow a determination of statistical significance. The number N will depend upon the assumption of a minimum number of overexpressing or underexpressing alleles in a sample (assumed herein to be at least 1%), and the further assumption that normal samples contain no overexpressing or under expressing alleles under detection. It is also assumed that a threshold differences between the ratios must be at least 0.5% (reflecting a minimum of 0.5% difference in expression of one reference RNA versus target RNA) for disease diagnosis. Based upon the foregoing assumptions, it is possible to determine how large N must be so that a detected difference in the ratios of less than 0.5% is truly a negative (i.e. no mutant subpopulation in the sample) result 99.9% of the time.

Figure 1B:
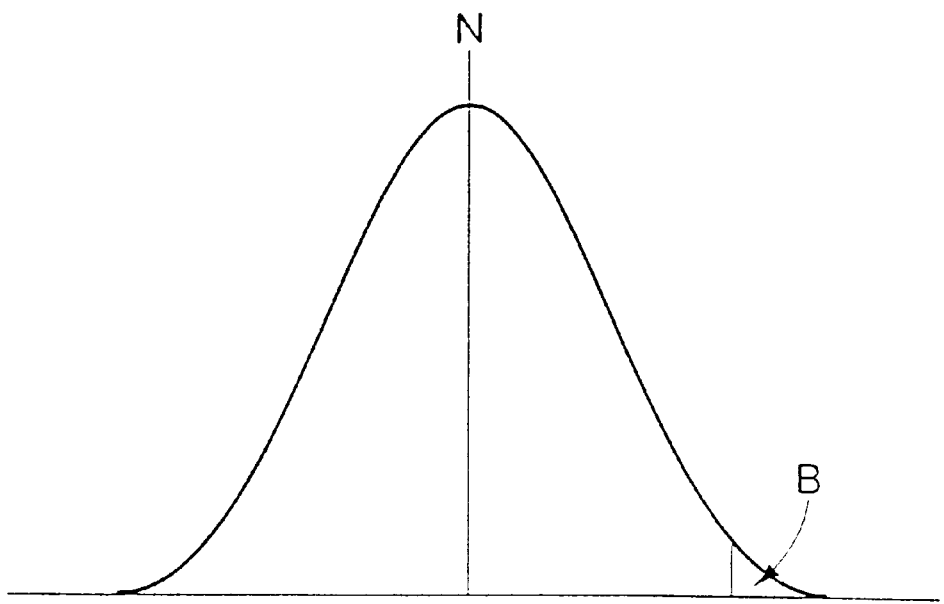

The calculation of N for specificity, then, is based upon the probability of one sample measurement being in the portion of the Gaussian distribution covering the lowest 3.16% of the population (the area marked "A" in FIG. 1A) and the probability that the other sample measurement is in the portion of the Gaussian distribution covering the highest 3.16% of the population (the area marked "B" in FIG. 1B). Since the two sample measurements are independent events, the probability of both events occurring simultaneously is approximately 0.001 or 0.1%. Thus, 93.68% of the Gaussian distribution (100%−2×3.16%) lies between the areas marked A and B in FIG. 3. Statistical tables indicate that such area is equivalent to 3.72 standard deviations. Accordingly, 0.5% N equals 3.72 sigma. Since sigma (the standard deviation) is equal to $\sqrt{N}$, the equation may be solved for N as 553,536. This means that if the lower of the two numbers representing reference and target is at least 553,536 and if the patient is normal, the difference between the numbers will be less than 0.5% about 99.9% of the time.

Figure 2:
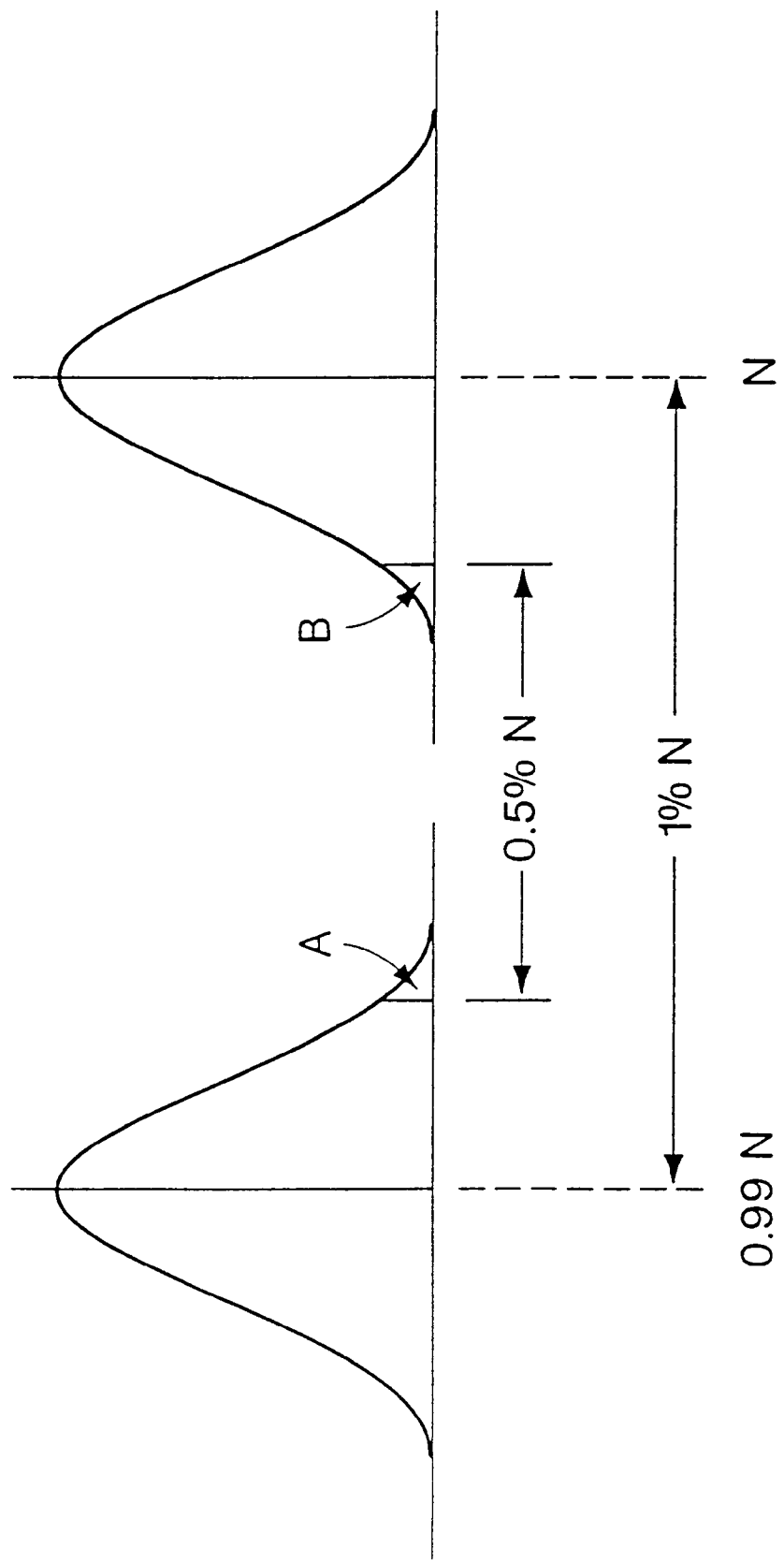
FIG. 2 is graph showing the probable values of N for a heterogeneous population of cells in which 1% of the cells are mutated.

To determine the minimum N required for 99% sensitivity a similar analysis is performed. One-tailed Gaussian distribution tables show that 1.28 standard deviations (sigma) from the mean cover 90% of the Gaussian distribution. Moreover, there is a 10% (the square root of 1%) probability that either the reference number of RNAs from a healthy sample or the reference number of RNAs from a patient sample will be in either the area marked "A" in FIG. 2 or in the area marked "B" in FIG. 2. If the two population means are a total of 1% different and if there must be a 0.5% difference in the number of target RNAs in a healthy sample and target RNAs in a patients sample, then the distance from either mean to the threshold for statistical significance is equivalent to 0.25% N (See FIG. 2) for 99% sensitivity. As shown in FIG. 2, 0.25% N corresponds to about 40% of one side of the Gaussian distribution. One-tailed statistical tables reveal that 40% of the Gaussian distribution corresponds to 1.28 standard deviations. Therefore, 1.28 sigma is equal to 0.0025N, and N equals 262,144. Thus, for samples from patients with a disease, the difference in the ratios will exceed 0.5% at least 99% of the time if the lower of the numbers is at least 262,144. Conversely, an erroneous negative diagnosis will be made only 1% of the time under these conditions.

In order to have both 99.9% specificity (avoidance of false positives) and 99% sensitivity (avoidance of false negatives), a sample with at least 553,536 (or roughly greater than 550,000) of both target and reference RNAs should be used. A difference of at least 0.5% between the numbers obtained is significant at a confidence level of 99.0% for sensitivity and a difference of less than 0.5% between the numbers is significant at a confidence level of 99.9% for specificity. As noted above, other standard statistical tests may be used in order to determine statistical significance and the foregoing represents one such test.

For purposes of exemplification, the following provides details of the use of methods according to the present invention in colon cancer detection. Inventive methods are especially useful in the early detection of an alteration in the level of expression of a disease-associated RNA. Accordingly, while exemplified in the following manner, the invention is not so limited and the skilled artisan will appreciate its wide range of applicability upon consideration thereof.

Methods for Detection of Cancer or Precancer

For exemplification, methods of the invention are used to detect an alteration in the expression of mRNA from the p53 tumor suppressor gene. Alterations in mRNA expression from the p53 gene are suspected to be associated with cancer, especially colorectal cancer. An mRNA sequence corresponding to the DNA coding region for p53 is reported as GenBank Accession No. M92424. Also for exemplification, beta-globin RNA is used as the reference RNA. The skilled artisan understands that methods described herein may be used to detect mutations in any gene and that detection of a p53 deletion is exemplary of such methods. RNA may optionally be isolated from a tissue or body fluid sample according to methods known in the art. See, Smith-Ravin, et al., Gut, 36: 81–86 (1995), incorporated by reference herein. Alternatively, cDNA may be used. A cDNA library is constructed according to methods known in the art.

Identical assays are performed on a patient sample, and on a sample known not to be affected by the disease (here, cancer) the diagnosis of which is desired. In each assay, the RNA may be sheared or cut into small fragments prior to counting. The size of the fragment is not critical, subject to the limitations described. One or more RNAase inhibitor also may be added prior to counting. First oligonucleotide probes which hybridize to at least a portion of the p53 mRNA and second oligonucleotide probes which hybridize to at least a portion of the beta-globin RNA are obtained. The probes are labeled with a detectable label, such as radioactive tags, fluorescein or detectable particles. Distinct labels for the probes are preferred.

Labeled probes are then exposed to sample under hybridization conditions. Such conditions are well-known in the art. See, e.g., Wallace, et al., *Nucleic Acids Res.*, 6:3543–3557 (1979), incorporated by reference herein. First and Second oligonucleotide probes that are distinctly labeled (i.e. with different radioactive isotopes, fluorescent means, or with beads of different size, See infra) are applied to a single aliquot of sample. After exposure of the probes to sample under hybridization conditions, sample is washed to remove any unhybridized probe. Thereafter, hybridized probes are detected separately for target and reference RNA. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

Next the ratio of p53 mRNA to beta-globin mRNA is determined in both the patient sample and the reference sample. Statistical significance may be determined by any known method. A preferred method is outlined above.

The determination of altered p53 RNA expression allows a clinician to recommend further treatment, such as endoscopy procedures, in order to further diagnose and, if necessary, treat the patient's condition. The following examples illustrate methods of the invention that allow direct quantification of hybridization events.

In order to achieve a higher degree of selectivity and specificity, counting is accomplished by annealing sequence-specific primers as described above, and subsequently conducting a single base extension assay using labeled non-extendible nucleic acids. Single base extension may be conducted either directly on reverse-transcribed DNA or on its corresponding cDNA. A single base primer extension reaction is performed by annealing an oligonucleotide primer to a complementary nucleic acid, and by extending the 3' end of the annealed primer with a chain terminating nucleotide that is added in a template directed reaction catalyzed by a DNA polymerase. The selectivity and sensitivity of a single base primer extension reaction are affected by the length of the oligonucleotide primer and the reaction conditions (e.g. annealing temperature, salt concentration).

The selectivity of a primer extension reaction reflects the amount of exact complementary hybridization between an oligonucleotide primer and a nucleic acid in a sample. A highly selective reaction promotes primer hybridization only to nucleic acids with an exact complementary sequence (i.e. there are no base mismatches between the hybridized primer and nucleic acid). In contrast, in a non selective reaction, the primer also hybridizes to nucleic acids with a partial complementary sequence (i.e. there are base mismatches between the hybridized primer and nucleic acid). In general, parameters which favor selective primer hybridization (for example shorter primers and higher annealing temperatures) result in a lower level of hybridized primer. Therefore, parameters which favor a selective single-base primer extension assay result in decreased sensitivity of the assay.

In a preferred embodiment, the reverse-transcribed DNA, or the corresponding double-stranded cDNA is amplified (e.g., by PCR) prior to performing a primer extension assay. In a highly-preferred embodiment, methods of the invention comprise conducting at least two cycles of a single-base extension reaction. By repeating the single-base extension reaction, methods of the invention increase the signal of a single-base primer extension assay, without reducing the selectivity of the assay. The cycling increases the signal, and the extension reaction can therefore be performed under highly selective conditions (for example, the primer is annealed at about or above its Tm).

In a preferred embodiment, methods of the invention are performed by annealing an excess of primer under conditions which favor exact hybridization, extending the hybridized primer, denaturing the extended primer, and repeating the annealing and extension reactions at least once. In a most preferred embodiment, the reaction cycle comprises a step of heat denaturation, and the polymerase is temperature stable (for example, Taq polymerase or Vent polymerase). Preferred primer lengths are between 10 and 100 nucleotides, more preferably between 10 and 50 nucleotides, and most preferably about 30 nucleotides Preferred hybridization conditions comprise annealing temperatures about or above the Tm of the oligonucleotide primer in the reaction. The Tm of an oligonucleotide primer is determined by its length and GC content, and is calculated using one of a number of formulas known in the art. Under standard annealing conditions, a preferred formula for a primer approximately 25 nucleotides long, is Tm (° C.)=4×(Number of Gs+Number of Cs)+2×(Number of As+Number of Ts).

In a preferred reaction, the annealing and denaturation steps are performed by changing the reaction temperature. In one embodiment of the invention, the primer is annealed at about the Tm for the primer, the temperature is raised to the optimal temperature for extension, the temperature is then raised to a denaturing temperature. In a more preferred embodiment of the invention, the reaction is cycled between the annealing temperature and the denaturing temperature, and the single base extension occurs during transition from annealing to denaturing conditions.

In a preferred embodiment of the invention, two or more cycles of extension are performed. In a more preferred embodiment, between 5 and 100 cycles are performed. In a further embodiment, between 10 and 50 cycles, and most preferably about 30 cycles are performed.

In a preferred embodiment of the invention, the nucleotide added to the 3' end of the primer in a template dependent reaction is a chain terminating nucleotide, for example a dideoxynucleotide. In a more preferred embodiment, the nucleotide is detectably labeled as discussed infra.

In a preferred embodiment, methods of the invention comprise conducting at least two cycles of single-base extension with a segmented primer. In a preferred embodiment, the segmented primer comprises a short first probe and a longer second probe capable of hybridizing to substantially contiguous portions of the target nucleic acid. The two probes are exposed to a sample under conditions that do not favor the hybridization of short first probe in the absence of longer second probe. Factors affecting hybridization are well known in the art and include temperature, ion concentration, pH, probe length, and probe GC content. A first probe, because of its small size, hybridizes numerous places in an average cDNA library. However, a small probe, for example, an 8-mer, has a low melting temperature ($T_m$) and a single base mismatch greatly exaggerates this instability. A second probe, on the other hand, is larger than the first probe and will have a higher $T_m$. A 20-mer second probe, for example, typically hybridizes with more stability than an 8-mer. However, because of the small thermodynamic differences in hybrid stability generated by single nucleotide changes, a longer probe will form a stable hybrid but will have a lower selectivity because it will tolerate nucleotide mismatches. Accordingly, under unfavorable hybridization conditions for the first probe (e.g., 10–40° C. above first probe $T_m$), the first probe hybridizes with high selectivity (i.e., hybridizes poorly to sequence with even a single mismatch), but forms unstable hybrids when it hybridizes alone (i.e., not in the presence of a second probe). The second probe will form a stable hybrid but will have a lower selectivity because of its tolerance of mismatches.

The extension reaction in the present invention will not occur absent contiguous hybridization of the first and second probes. A first (proximal) probe alone is not a primer for template-based nucleic acid extension because it will not form a stable hybrid under the reaction conditions used in the assay. Preferably, the first probe comprises between about 5 and about 10 nucleotides. The first probe hybridizes adjacent to a nucleic acid suspected to be mutated. A second (distal) probe in mutation identification methods of the invention hybridizes upstream of the first probe and to a substantially contiguous region of the target (template). The second probe alone is not a primer of template-based nucleic acid extension because it comprises a 3' non-extendible nucleotide. The second probe is larger than the first probe, and is preferably between about 15 and about 100 nucleotides in length.

According to methods of the invention, template-dependent extension takes place only when a first probe hybridizes next to a second probe. When this happens, the short first probe hybridizes immediately adjacent to the site of the suspected single base mutation. The second probe hybridizes in close proximity to the 5' end of the first probe. The presence of the two probes together increases stability due to cooperative binding effects. Together, the two probes are recognized by polymerase as a primer. This system takes advantage of the high selectivity of a short probe and the hybridization stability imparted by a longer probe in order to generate a primer that hybridizes with the selectivity of a short probe and the stability of a long probe. Accordingly, there is essentially no false priming with segmented primers. Since the tolerance of mismatches by the longer second probe will not generate false signals, several segmented primers can be assayed in the same reaction, as long as the hybridization conditions do not permit the extension of short first probes in the absence of the corresponding longer second probes By requiring hybridization of the two probes, false positive signals are reduced or eliminated. As such, the use of segmented oligonucleotides eliminates the need for careful optimization of hybridization conditions for individual probes, as presently required in the art, and permits extensive multiplexing. Several segmented oligonucleotides can be used to probe several target sequences assayed in the same reaction, as long as the hybridization conditions do not permit stable hybridization of short first probes in the absence of the corresponding longer second probes.

The first and second probes hybridize to substantially contiguous portions of the target. For purposes of the present invention, substantially contiguous portions are those that are close enough together to allow hybridized first and second probes to function as a single probe (e.g., as a primer of nucleic acid extension). Substantially contiguous portions are preferably between zero (i.e., exactly contiguous so there is no space between the portions) nucleotides and about one nucleotide apart. A linker is preferably used where the first and second probes are separated by two or more nucleotides, provided the linker does not interfere with the assay (e.g., nucleic acid extension reaction). Such linkers are known in the art and include, for example, peptide nucleic acids, DNA binding proteins, and ligation. It has now been realized that the adjacent probes bind cooperatively so that the longer, second probe imparts stability on the shorter, first probe. However, the stability imparted by the second probe does not overcome the selectivity (i.e., intolerance of mismatches) of the first probe. Therefore, methods of the invention take advantage of the high selectivity of the short first probe and the hybridization stability imparted by the longer second probe.

In an alternative preferred embodiment, a segmented oligonucleotide comprises a series of first probes, wherein sufficient stability is only obtained when all members of the segmented oligonucleotide simultaneously hybridize to substantially contiguous portions of a nucleic acid. It has now been realized that, although short probes exhibit transient, unstable hybridization, adjacent short probes bind cooperatively and with greater stability than each individual probe. Together, a series of adjacently-hybridized first probes will have greater stability than individual probes or a subset of probes in the series. For example, in an extension reaction with a segmented primer comprising a series of three first probes (i.e., three short probes with no terminal nucleotide capable of hybridizing to a substantially contiguous portion of a nucleic acid upstream of the target nucleic acid), the concurrent hybridization of the three probes will generate sufficient cooperative stability for the three probes to prime nucleic acid extension and the 3' short probe will be extended. Thus, segmented probes comprising a series of short first probes offer the high selectivity (i.e., intolerance of mismatches) of short probes and the stability of longer probes.

In a preferred embodiment, several cycles of extension reactions are conducted in order to amplify the assay signal. Extension reactions are conducted in the presence of an excess of first and second probes, labeled dNTPs or ddNTPs, and heat-stable polymerase. Once an extension reaction is completed, the first and second probes bound to target nucleic acids are dissociated by heating the reaction mixture above the melting temperature of the hybrids. The reaction mixture is then cooled below the melting temperature of the hybrids and first and second probes permitted to associate with target nucleic acids for another extension reaction. In a preferred embodiment, 10 to 50 cycles of extension reactions are conducted. In a most preferred embodiment, 30 cycles of extension reactions are conducted.

Labeled ddNTPs or dNTPs preferably comprise a "detection moiety" which facilitates detection of the extended primers, or extended short first probes in a segmented primer reaction. Detection moieties are selected from the group consisting of fluorescent, luminescent or radioactive labels, enzymes, haptens, and other chemical tags such as biotin which allow for easy detection of labeled extension products. Fluorescent labels such as the dansyl group, fluorescein and substituted fluorescein derivatives, acridine derivatives, coumarin derivatives, pthalocyanines, tetramethylrhodamine, Texas Red®, 9-(carboxyethyl)-3-hydroxy-6-oxo-6H-xanthenes, DABCYL® and BODIPY® (Molecular Probes, Eugene, Oreg.), for example, are particularly advantageous for the methods described herein. Such labels are routinely used with automated instrumentation for simultaneous high throughput analysis of multiple samples.

In a preferred embodiment, primers or first probes comprise a "separation moiety." Such separation moiety is, for example, hapten, biotin, or digoxigenin. These primers or first probes, comprising a separation moiety, are isolated from the reaction mixture by immobilization on a solid-phase matrix having affinity for the separation moiety (e.g., coated with anti-hapten, avidin, streptavidin, or anti-digoxigenin). Non-limiting examples of matrices suitable for use in the present invention include nitrocellulose or nylon filters, glass beads, magnetic beads coated with agents for affinity capture, treated or untreated microtiter plates, and the like.

In a preferred embodiment, the separation moiety is incorporated in the labeled ddNTPs or dNTPs. By denaturing hybridized primers or probes, and immobilizing primers or first probes extended with a labeled ddNTP or dNTP to a solid matrix, labeled primers or labeled first probes are isolated from unextended primers or unextended first probes and second probes, and primers or first probes extended with an unlabeled ddNTPs by one or more washing steps.

In an alternative preferred embodiment, the separation moiety is incorporated in the primers or first probes, provided the separation moiety does not interfere with the first primer's or probe's ability to hybridize with template and be extended. Eluted primers or first probes are immobilized to a solid support and can be isolated from eluted second probes by one or more washing steps.

Alternatively, the presence of primers or first probes that have been extended with a labeled terminal nucleotide may be determined without eluting hybridized primers or probes. The methods for detection will depend upon the label or tag incorporated into the primers or first probes. For example, radioactively labeled or chemiluminescent first probes that have bound to the target nucleic acid can be detected by exposure of the filter to X-ray film. Alternatively, primers or first probes containing a fluorescent label can be detected by excitation with a laser or lamp-based system at the specific absorption wavelength of the fluorescent reporter.

In an alternative embodiment, the bound primers or first and second probes are eluted from a matrix-bound target nucleic acid (see below). Elution may be accomplished by any means known in the art that destabilizes nucleic acid hybrids (i.e., lowering salt, raising temperature, exposure to formamide, alkali, etc.). In a preferred embodiment, the bound oligonucleotide probes are eluted by incubating the target nucleic acid-segmented primer complexes in water, and heating the reaction above the melting temperature of the hybrids.

Deoxynucleotides may be used as the detectable single extended base in any of the reactions described above that require single base extension. However, in such methods, the extension reaction must be stopped after addition of the single deoxynucleotide. Such methods may be employed regardless of whether a specific mutation is known (i.e., C→G). Moreover, the extension reaction need not be terminated after the addition of only one deoxynucleotide if only one labeled species of deoxynucleotide is made available in the sample for detection of the single base mutation. This method may actually enhance signal if there is a nucleotide repeat including the interrogated single base position.

In a preferred embodiment, target nucleic acids are immobilized to a solid support prior to exposing the target nucleic acids to primers or segmented primers and conducting an extension reaction. Once the nucleic acid samples are immobilized, the samples are washed to remove non-immobilized materials. The nucleic acid samples are then exposed to one or more set of primers or segmented primers according to the invention. Once the single-base extension reaction is completed, the primers or first probes extended with a labeled ddNTP or dNTP are preferably isolated from unextended probes and probes extended with an unlabeled ddNTPs or dNTP. Bound primers or first and second probes are eluted from the support-bound target nucleic acid. Elution may be accomplished by any means known in the art that destabilizes nucleic acid hybrids (i.e., lowering salt, raising temperature, exposure to formiamide, alkali, etc.). In a preferred embodiment, the first and second probes bound to target nucleic acids are dissociated by incubating the target nucleic acid-segmented primer complexes in water, and heating the reaction above the melting temperature of the hybrids and the extended first probes are isolated. In an alternative preferred embodiment, the extension reaction is conducted in an aqueous solution. Once the single-base extension reaction is completed, the oligonucleotide probes are dissociated from target nucleic acids and the extended first probes are isolated. In an alternative embodiment, the nucleic acids remain in aqueous phase.

Finally, methods of the invention comprise isolating and sequencing the extended first probes. A "separation moiety" such as, for example, hapten, biotin, or digoxigenin is used for the isolation of extended first probes. In a preferred embodiment, first probes comprising a separation moiety are immobilized to a solid support having affinity for the separation moiety (e.g., coated with anti-hapten, avidin, streptavidin, or anti-digoxigenin). Non-limiting examples of supports suitable for use in the present invention include nitrocellulose or nylon filters, glass beads, magnetic beads coated with agents for affinity capture, treated or untreated microtiter plates, and the like.

What is claimed is:

1. A method for disease diagnosis, comprising the steps of:

comparing a first ratio, obtained from a sample comprising non-diseased cells, of a reference RNA, the expression level of which is not expected to be altered in a diseased cell, to a target RNA, the expression level of which is expected to be altered in a disease cell, with a second ratio, obtained from a test sample, of said reference RNA to said target RNA; and determining whether there is a statistically-significant difference between said first ratio and said second ratio, the presence of statistically-significant difference being indicative of the presence of diseased cells in said test sample.

2. A method for detecting a difference in RNA expression between first and second samples, comprising the steps of comparing a ratio of a first RNA to a second RNA in a first sample with said ratio in a second sample.

3. A method for identifying a gene, the expression of which is associated with a disease, comprising the steps of comparing a ratio, in a disease sample, of an RNA expression product of said gene to an RNA expression product of a reference gene that is not affected by disease, with said ratio in a non-diseased sample, the presence of a statistically-significant difference between said ratios being indicative of a gene, the expression of which is associated with the disease.

4. A method for determining predisposition to a disease in a patient, comprising the step of determining a ratio of RNA expressed by a paternal allele to RNA expressed by a maternal allele; wherein said patient is predisposed to said disease if there is a statistically-significant difference between said ratio and 1.0.

5. A method for disease diagnosis, comprising the steps of:

(a) counting molecules of a first RNA, the expression of which is not different in a diseased cell as compared to a non-diseased cell;

(b) counting molecules of a second RNA, the expression of which is expected to be different in a diseased cell as compared to a non-diseased cell;

(c) determining whether a statistically-significant difference exists between numbers of said first RNA and said second RNA, the presence of a statistically-significant difference being indicative of a disease.

* * * * *